United States Patent [19]

Seitz et al.

[11] 3,967,934

[45] *July 6, 1976

[54] PROTHROMBIN TIMER

[75] Inventors: Lamont J. Seitz, Huntington Beach; John G. Bowen, South Pasadena, both of Calif.

[73] Assignee: Baxter Laboratories, Inc., Deerfield, Ill.

[ * ] Notice: The portion of the term of this patent subsequent to Jan. 16, 1989, has been disclaimed.

[22] Filed: June 25, 1971

[21] Appl. No.: 156,740

Related U.S. Application Data

[63] Continuation-in-part of Ser. No. 846,992, June 13, 1969, Pat. No. 3,635,678, which is a continuation-in-part of Ser. No. 738,382, June 17, 1968, abandoned.

[52] U.S. Cl................................ 23/253 R; 23/259; 73/57; 73/59; 73/64.1
[51] Int. Cl.².................. G01N 11/10; G01N 33/16
[58] Field of Search.......... 23/230 R, 230 B, 253 R, 23/259; 73/57, 59, 64.1

[56] References Cited
UNITED STATES PATENTS

| | | |
|---|---|---|
| 2,957,338 | 10/1960 | Kennedy et al.......................... 73/54 |
| 3,267,363 | 8/1966 | Young............................ 23/253 R X |
| 3,271,112 | 9/1966 | Williams et al.................... 23/253 R |
| 3,375,705 | 4/1968 | Kim........................................ 73/57 |
| 3,443,419 | 5/1969 | Guitroy et al......................... 73/64.1 |
| 3,520,659 | 7/1970 | Steinberg et al............... 23/253 R X |

*Primary Examiner*—Joseph Scovronek
*Attorney, Agent, or Firm*—Lawrence W. Flynn; Louis Altman

[57] ABSTRACT

A system and method is provided which has the general capabilities of measuring the speed of coagulation, congealing or solidification of a fluid sample, and which has particular utility in the measurement of the time required by a sample under test to increase viscosity to a particular level. The system and method to be described is predicated on a viscosity principle, and it includes a movable magnetic member suspended in the fluid sample and which changes position when the sample achieves a predetermined degree of viscosity. The change in position of the aforesaid member is photoelectrically or electromagnetically detected, and the time at which the change occurs, is used in the determination of the time required, for example, for the sample to form a fibrin clot, in a blood or plasma sample or to effect a particular reaction causing solidification or congealing of the sample.

1 Claim, 8 Drawing Figures

U.S. Patent   July 6, 1976   Sheet 1 of 3   3,967,934
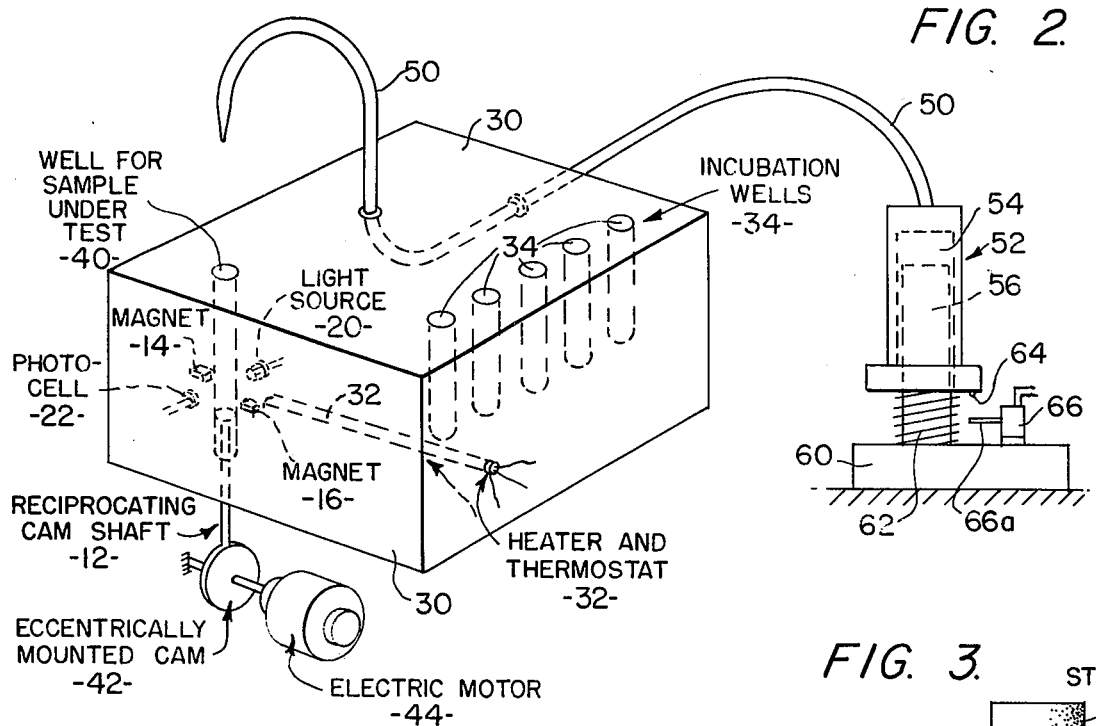
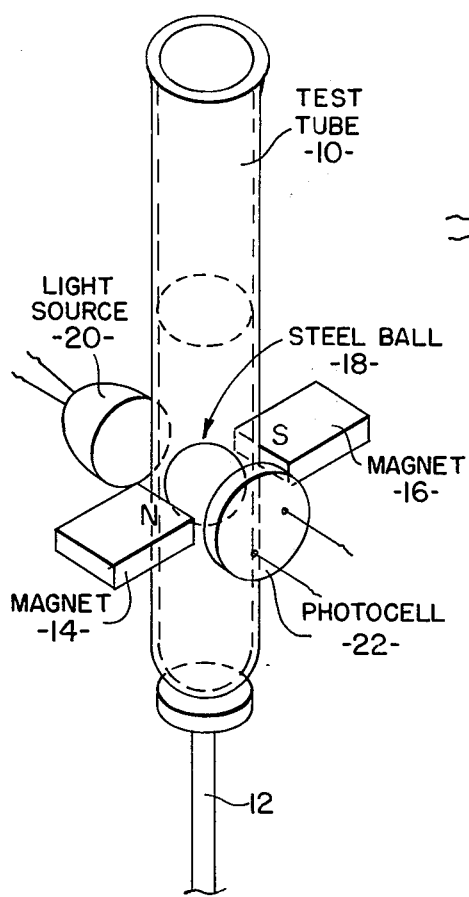
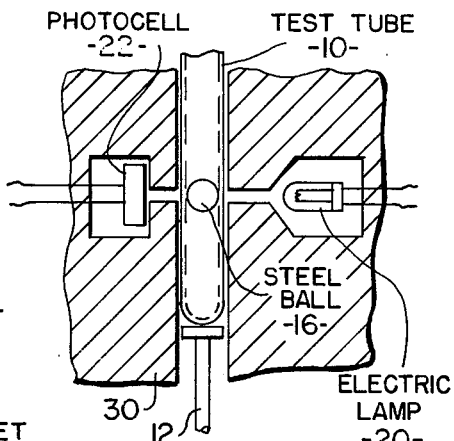
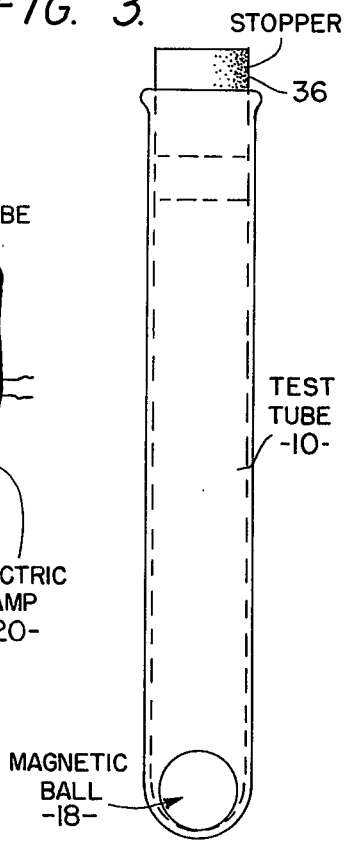
INVENTORS
LAMONT J. SEITZ &
JOHN G. BOWEN
BY   *Scott J. Meyer*
ATTORNEY

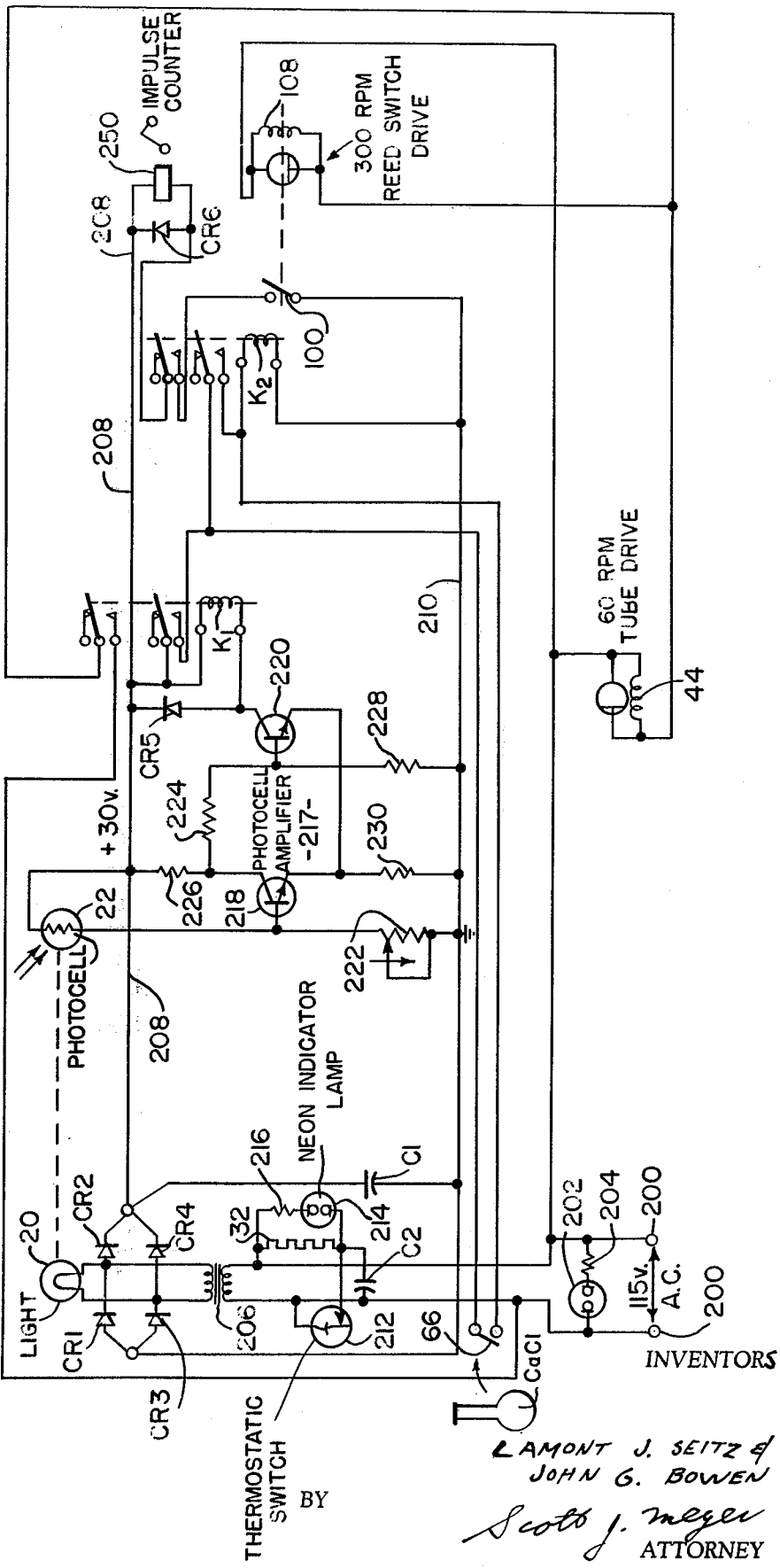

INVENTORS
LAMONT J. SEITZ &
JOHN G. BOWEN

BY Scott J Meyer
ATTORNEY

PROTHROMBIN TIMER

CROSS-REFERENCES TO RELATED APPLICATIONS

This is a continuation-in-part of co-pending application Ser. No. 846,992, filed June 13, 1969 and now issued as U.S. Pat. No. 3,635,678 on Jan. 18, 1972, which in turn is a continuation-in-part of co-pending application Ser. No. 738,382, filed June 17, 1968, now abandoned.

This invention relates to a clot timing system and more particularly to a prothrombin timer which determines the prothrombin time of blood samples.

The importance and significance of blood coagulation has long been recognized. In recent years, there has been a great amount of research into the complexities of coagulation. Much of the present interest in coagulation has been centered upon the disease of hemophilia and other cengenital or acquired bleeding disorders.

Before proper therapy can be initiated for a bleeding disorder in the patient, the cause of the bleeding must first be understood. These causes can be determined by different tests involving the coagulation of the patient's blood. These tests involve, for example, the determination of the time required by the patient's blood to manifest a clotting condition, generally known as the prothrombin time determination.

In the past, the incidence of clotting of the blood sample was usually detected by visual means. However, instruments for automatically detecting the clot formation have also been proposed in the prior art. These instruments, for example, detect the clot formation in the blood or plasma sample by photometric means, or by resistance or capacitance changes in an electric circuit. However, the prior art systems for the most part suffer from one drawback or another. For example, most of the prior art instruments have questionable temperature control, and have time resolutions no better than 0.6 seconds. In addition, the usual prior art instruments are rather inconvenient to use, since they require frequent cleaning, adjustments, and the like.

In other reactions where the time of congealing or solidification is of interest, the conventional viscosimeter is used to detect and measure a reaction rate or time to reach a certain viscosity. These, however, are usually not as uniform or precise as are required in sensitive reactions as for instance in polymerization reactions, precipitation of viscous components of solutions, or in other diagnostic tests in which there is a sudden or dramatic increase in viscosity. The conventional tests now in use suffer from the same problems extant with the clot timing tests mentioned above.

The improved prothrombin timing system and method of the present invention, as mentioned briefly above, detects in a predetermined manner any increase in clotting in a blood or plasma sample by sensing predetermined changes in the viscosity of the sample. In one embodiment to be described, for example, a freely movable magnetic member such as a ball or disc composed of appropriate ferromagnetic material, such as steel, is introduced into the fluid sample held in a container or other such holding means. The sample is placed within a magnetic field which tends to hold the movable magnetic member in a fixed position as the sample and its holding means are reciprocated. This condition obtains so long as the viscosity of the sample remains below a predetermined threshold. However, when the increased viscosity of the fluid sample is sufficient to enable the reciprocating fluid to force the movable magnetic member away from its fixed position, and against the magnetic force tending to hold it in its fixed position, the change in the position of the movable magnetic member in the sample is detected and the time can be measured by any convenient timer means.

The resultant movement of the movable magnetic member can be sensed by photoelectric means, as will be described hereinafter. As an alternative, said movement can be electromagnetically detected by sensing the resulting change in magnetic reluctance of the system as the movable magnetic member is so moved. In either event, the precise time for the reaction in the sample to thicken, congeal or solidify can be measured by the apparatus of the invention. It will be appreciated, of course, that the sample itself may be held stationary, and the magnetic field moved back and forth to achieve the same result, or that other such relative movement of the sample holding means and the magnetic member in the liquid sample can be provided by means external to the sample holding means magnetically coupled to the movable magnetic member.

The system, apparatus and method to be described is advantageous in that tests can be conducted in conjunction with disposable test tubes for the samples, or other such sample holding means, each containing a movable magnetic member. The test tubes can be held at a predetermined temperature in the apparatus of the invention by suitable supporting means, before and when the actual test is made. After each test, the test tube, its magnetic member, and the remaining contents in the tube may all be disposed of, so that no cleaning operations are involved.

In the clot timing test as described, a precisely controlled heating system is preferably used in the apparatus, so that the temperature can be held, for example, at normal body temperature of 37° C ± 0.5° for blood or plasma tests. The apparatus to be described also inherently provides adequate mixing of the sample during the test. For precise time measurements, the start of the time interval is automatically synchronized with the moment the test is initiated. A constructed embodiment of the apparatus of the invention exhibits capabilities of providing time resolutions to 0.1 second, and a detection sensitivity down to 5% activity.

Many factors interact in a complex manner in the blood or plasma sample from the first step in the coagulation process to the final formation of the fibrin clot. The coagulation process itself undergoes three separate stages, for example. During the first stage, several plasma factors react with platelets in the presence of a source of calcium ions, such as calcium chloride, to generate thromboplastin. The second stage involves the conversion of prothrombin to thrombin. Once formed, the process enters the third stage during which the thrombin rapidly converts soluble fibrinogen to insoluble fibrin. In so doing, the thrombin catalyzes the spreading of fibrinopeptides from the fibrinogen molecule, allowing the latter to polymerize and form the fibrin clot.

Any source of soluble, ionizable calcium salts are suitable as the aforesaid source of calcium ions in the clot timing technique of this invention. Calcium chloride is preferred by most researchers but others prefer other, soluble ionizable calcium compounds. However, care must be exercised as, for instance, the oxalate salt is insoluble and not ionizable and the citrate salt is, for example, not ionizable even though soluble.

In making coagulation tests, the first stage can be by-passed by adding tissue thromboplastin and calcium chloride to the blood or plasma sample. Such tests measure the prothrombin time of the sample. The original one-stage prothrombin time test was devised by Quick *Amer. Journ. Clin. Pathol.* 10, 222, (1940). This test was originally believed to measure prothrombin activity only. It has since been found that the Quick test actually measures all the factors involved in the latter coagulation stages described in the preceeding paragraph. Nevertheless, the Quick test has proven to be still a useful tool in evaluating anti-coagulant therapy. However, if prothrombin is to be measured specifically, a two-stage test is used in which prothrombinfree plasma is added to the sample, in the method described by Ware and Seegers, *Amer. Journ. Clin. Pathol.* 19, 471 (1949).

The system, method and apparatus of the present invention can be used in conjunction with either of the aforesaid tests, or in other tests involving fluid viscosity. For example, in addition to the Quick test referred to above, in which liquid thromboplastin forms the additional reagent, the system, apparatus and method of the invention can also be applied to the "PTT" test involving kaolin activated liquid partial thromboplastin; the differential "PTT" test involving AHF reagent, PTC reagent, and kaolin activated liquid partial thromboplastin; the modified Owren test involving prothrombin-free beef plasma and liquid thromboplastin; the factor VIII (AHF) assay involving kaolin activated liquid partial thromboplastin, factor VIII deficient substrate, and a diluting fluid such as "Veronal" buffer; and the factor IX (PTC) assay involving kaolin activated liquid partial thromboplastin, factor IX deficient substrate, and a diluting fluid such as "Veronal" buffer; as are described by Biggs and MacFarlane in "Human Blood Coagulation and its Disorders", Third Edition, F. A. Davis Company, Philadelphia, Penn. (1962).

All the aforesaid tests can involve the start of the time measurement as the calcium chloride solution is added. The strength of the calcium chloride solution, however, can differ from test to test, for example, 0.02 molar to 0.03 molar. For each of the tests, for example, the test tubes of the suitable reagent are provided, each incorporating a movable magnetic member. The blood or plasma samples to be tested are pipetted into the test tubes containing the suitable reagent after the test tubes have been placed in the apparatus, and are then incubated at the test temperature. The test in each instance is started by the addition of the calcium chloride solution, and the apparatus to be described herein is constructed so that the timer starts at the exact moment the calcium chloride is added to the sample. The timer is subsequently stopped by the change of viscosity in the sample, for example, due to the first appearance of strands of fibrin clot.

In an actual test to be described, the prothrombin time of a combination of blood plasma, calcium ions and thromboplastin is measured. The presence of calcium ions, either as calcium chloride or other ionizable and soluble calcium salt, is essential to the clotting action in the particular test, as measured by the apparatus. An optimum concentration of calcium ions provides the shortest and most accurate clotting time. This is normally about 1/50 molar as standardized with 1 cc of 3.8% sodium citrate solution and 9 milliliters of whole blood. As mentioned above, in a specific embodiment of the invention to be described, the thromboplastin is pre-packaged as a disposable item in a test tube, complete with a movable magnetic member and stopper, for each blood or plasma test. The blood sample of the patient is initially mixed with the thromboplastin in the test tube. However, the calcium chloride ingredient is omitted from the pre-packaged thromboplastin, and the calcium chloride solution is pipetted into the test tube at the initiation of the test. The fibrin clot is subsequently detected by the means described above, at which time the timer is deactuated and stops and provides an indication of the prothrombin time. In some instances, of course, the calcium chloride may be included in the pre-packaged thromboplastin. Moreover, in some laboratories, the thromboplastin may be carried as a stable item, and introduced into the test tube and magnetic member combination in the laboratory itself, just prior to making the tests.

While we have described the apparatus and method of this invention as having particular utility in the prothrombin or clotting times of blood, its ready application to other tests will be obvious to those having particular requirements for measuring the precise time for a particular reaction to occur which is characterized by an increase in viscosity of the sample to a point where the viscosity is sufficient to jell, congeal, or thicken the sample enough to move the magnetic member out of its predetermined position in the magnetic field as the sample container is reciprocated relative to the field.

In jell time measurements for example, and in polymerization action or tests, the same basic principle is employed, and any particular combination of reagents or conditions can be employed as are conventional in that test with only the clearance between the movable magnetic member and the sample holder being considered in relation to the intensity or speed of the viscosity increase of the reaction or physical phenomena being measured. In some reactions, for example, additional polymerization reactions or jell formation can take place with such a dramatic increase in viscosity that gross clearance can be provided between the movable magnetic member and the wall of the sample holder because the magnetic member will become almost imbedded and immobile in the sample that clearance is immaterial. In other reactions, however, a close tolerance between the walls of the sample holder and the movable magnetic member may be desired such that a precise viscosity is necessary for the magnetic member to be moved out of its predetermined location in the magnetic field. Thus each specific test may require a different clearance or at least consideration of the normal viscosity increase incident to that test and a selection of the most optimum clearance for that test. In the following discussion, clearance will be considered relative to the clot timing test.

BRIEF DESCRIPTION OF THE DRAWINGS

FIG. 1 is a perspective schematic representation showing the principles upon which the embodiment of the invention to be described is predicted;

FIG. 2 is a perspective view of the apparatus of the invention, in somewhat schematic form, and representing one embodiment;

FIG. 3 is a pre-packaged test tube-magnetic member assembly in which the reagent for the sample to be tested is contained;

FIG. 4 is an enlarged fragmentary section of a portion of the apparatus of FIG. 2 and showing the photoelectric sensing system which is used in the apparatus of FIG. 2;

FIG. 5 is an elevational view of a suitable pulse generator which can be used in conjunction with the apparatus of FIG. 2;

FIG. 6 is a diagram of the electrical control system associated with the apparatus of FIG. 2.

DETAILED DESCRIPTION OF AN ILLUSTRATIVE EMBODIMENT

Figure 7:
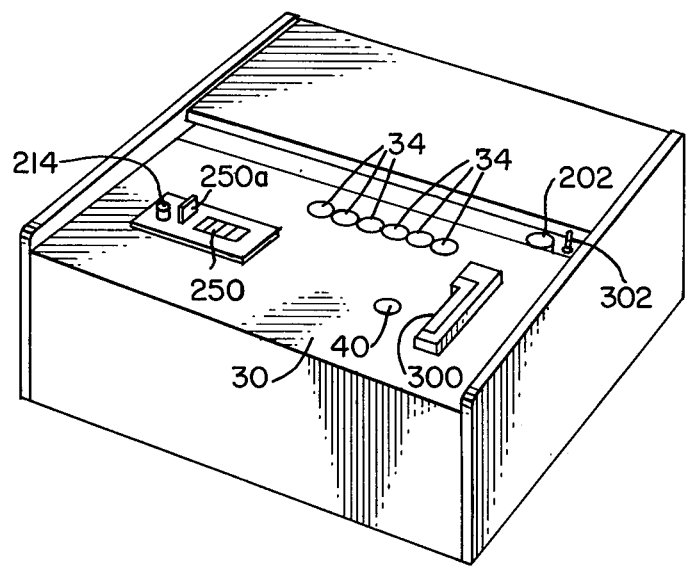
FIGS. 7 and 8 show an appropriate housing for the apparatus, the housing being shown closed in FIG. 7 and open in FIG. 8.

As shown in FIG. 1, a test tube 10 containing the fluid to be tested is supported in the apparatus on a piston, or cam shaft, 12. The piston 12 moves reciprocally in the vertical direction in FIG. 1, so that the test tube 10 is moved up and down with the piston. In carrying out the concepts of the present invention, a magnetic field is established through the test tube. This magnetic field can be created by means of a magnetic field source such as, for example, a pair of stationary bar magnets 14 and 16. A magnetic member 18 is suspended in the fluid within the test tube 10. This member can, for example, be in the form of a ball of stainless steel, or other appropriate magnetic material. For example, the ball may be a chromium-plated member whose interior is formed of an appropriate magnetic material. In a constructed embodiment of the invention, the magnetic member 18 has the configuration of a stainless steel ball, and a diameter of 0.187 inches. The test tube 10, on the other hand, is a precision bore test tube in the constructed embodiment, whose bore diameter is 0.199 inches ± 0.004 inches. The excursion rate of the test tube by the piston 12 in the constructed embodiment is 120 complete cycles per minute, and the excursion amplitude is controlled so that the ball moves relative to the liquid in the test tube a maximum amount without breaking the surface of the liquid. Should the ball break through the meniscus at the surface of the liquid, air is entrained within the liquid and bubbles are formed.

It will be appreciated that so long as the viscosity of the liquid in the test tube is below a predetermined threshold, the magnetic member 18 is held stationary by the magnetic field established by the magnets 14 and 16, as the liquid moves up and down with the test tube 10. However, when the viscosity of the liquid exceeds a certain threshold due, for example, to the formation of a solid fibrin clot, the liquid draws the magnetic member 18 with it out of the magnetic field, and against the force of the magnetic field. The resulting change in the position of the magnetic member 18 can be sensed by directing a light beam through the test tube from a light source 20, the light beam being detected by a photocell 22 when the magnetic member 18 moves its position.

That is, the light source 20 and photocell 22 can be mounted in the same plane as the magnets 14 and 16, and disposed at right angles thereto, as shown in FIG. 1. So long as the magnetic member 18 is held in the magnetic field established by the magnets 14 and 16, it blocks the light to the photocell. However, when the viscosity of the fluid in the test tube exceeds the predetermined threshold, such as by clotting, congealing or solidifying, the magnetic member 18 is moved from its illustrated position, so that the light from the source 20 strikes the photocell 22, causing the photocell to generate a signal. This signal which is derived in response to the relative movement between the magnetic member 18 and the magnetic field source signifies the end point in determining the prothrombin time.

The concept shown in FIG. 1 permits prothrombin times conveniently to be determined in blood or plasma samples. For example, the test tube 10 may be disposable, together with its magnetic member 18. Initially, a quantity of thromboplastin is inserted into the test tube, of the order, for example, of 1/10th milliliter. The tube is then equipped with a stopper. Before the test, the stopper may be removed and an equal quantity of blood or plasma sample, for example, may be pipetted into the test tube. Then, at the instant the timing interval is initiated, a like amount of calcium solution can be introduced into the test tube to start the coagulation reaction. During the test, the magnetic member 18 moves relative to the liquid in the test tube, from the bottom of the liquid to the meniscus, for example, as the test tube is moved. In this way, the magnetic member 18 additionally performs a thorough stirring function. The test tube, ball and stopper are shown in FIG. 3, the stopper being designated as 36.

The subsequent movement of the magnetic member 18 out of the magnetic field upon the formation of the fibrin clot, causes the photocell 22 to generate an output, and this output can be used to terminate the timing interval, so that the prothrombin time can be determined. As mentioned above, as an alternative, the movement of the magnetic member 18 relative to the liquid can be detected by measuring the resulting change in reluctance in the magnetic circuit, rather than by the photocell 22, if desired. Also, although a reciprocal motion is shown in the drawing and described above, other suitable motion of the liquid, such as a circular movement, for example, can be used with respect to the ball 18.

Appropriate apparatus for carrying out the concept shown in FIG. 1 is illustrated in FIG. 2. The apparatus of FIG. 2 includes, for example, a metallic block 30. An electric heater and thermostat unit 32 is inserted into the block 30, and when the heater is energized, the thermostat unit serves to cause it to maintain the block at a predetermined temperature. This temperature for plasma and blood tests, for example, is preferably 37° C, which corresponds to the normal body temperature. The control can be sufficiently precise so that the block is maintained at that temperature to within 0.5° C.

A series of incubation wells 34 or other sample holding compartments can be provided in the block 30, and these wells can serve as an appropriate storage means for test tubes of the samples to be tested, and also as a storage means for a test tube of the calcium chloride solution which is used in the tests, as described above, since it too should be maintained at the test temperature. For example, prior to the initiation of the test, a group of pre-packaged test tubes 10, shown in FIG. 3, each containing its magnetic ball 18 and stopper 36, and each filled with, for example, 1/10th of a milliliter of thromboplastin, can be removed from a refrigerator and placed in the incubation well 34.

The different blood samples to be tested can then be pipetted into the various test tubes in the wells 34, with 1/10th of a milliliter being placed in each test tube. The test tubes are left in the incubation wells for a sufficient incubation interval so that the liquids therein can be brought to the test temperature of 37° C. In a typical test, for example, and as mentioned above, it is usual for each test tube to contain 1/10th of a milliliter of plasma, 1/10th of a milliliter of thromboplastin, and subsequently 1/10th of a milliliter of calcium chloride solution is added to initiate the test.

When a test is to be made, one of the test tubes 10 is removed from its incubation well 34 and is placed in a further well 40 or similar such sample holding compartment, which extends through the block 30 near the magnetic field source. The aforesaid piston, or reciprocating cam shaft 12 is positioned in the well 40, and the shaft rests on the edge of an eccentrically mounted cam 42. The cam 42 is driven, for example, by an electric motor 44. It will be appreciated that when the electric motor 44 is energized to drive the eccentric cam 42, the cam shaft 12 is caused to move up and down in the well 40. Then, when a test tube 10 is inserted down into the well, it rests on top of the shaft 12 in the manner shown in FIG. 1, for example, to move with the shaft up and down in the well 40.

The magnets 14 and 16, together with the light source 20 and photocell 22, are mounted in appropriate tunnels in the block 30. These tunnels can have the configuration shown in FIG. 4, for example, with respect to the photocell 22 and light source 20, the latter being formed by an electric lamp. The diameter of the tunnels from the photocell and light source are preferably made slightly smaller than the diameter of the magnetic member 18, so that slight movements of the magnetic member will not cause the photocell to be activated. For example, in the construction embodiment, the tunnels have a diameter of one-eighth of an inch, whereas the magnetic member 18, or ball has a diameter, as mentioned above, of 0.187 inches.

The electrical control system of the apparatus can be such that immediately upon the placement into the well 40 of the test tube containing the sample to be tested and containing the magnetic member 18, the resulting blocking of the light beam incident on the photocell 22 by the ball causes the electric motor 44 to be activated, so that the test tube moves up and down in the well 40. However, the coagulation reaction does not begin until the calcium chloride solution is added to the liquid in the test tube. This calcium chloride solution addition can be made, for example, by means of a flexible pipette tube 50 which, for example, can be activated by a pipette mechanism 52. The pipette mechanism 52 can be similar to that described in U.S. Pat. No. 3,236,423. It comprises essentially an outer cylinder 54 and an inner rod 56. The rod 56 is mounted on a base 60, and the cylinder 54 is mounted over the rod in coaxial relationship therewith. A spring 62, for example, biases the cylinder into an upper position. The tube 50 is coupled into the interior of the cylinder 54 through the upper end of the cylinder.

The outer cylinder 54 is first pressed down to a predetermined position, established by an appropriate stop rod (not shown), and the free end of the flexible tube can be inserted into the test tube which contains the calcium chloride, and which can be stored in one of the incubation wells 34. The cylinder 54 is then released causing a precisely metered amount of the calcium chloride solution to be drawn into the cylinder 54. Then, the free end of the flexible tube 50 is moved over the top of the test tube 10 which is moving reciprocally in the well 40, and the cylinder 54 is moved down to the base 60 against the bias of the spring 62. This latter movement of the cylinder causes the calcium chloride solution to be discharged from the cylinder 54 into the reciprocating test tube in the well 40. At the same time, a stop 64 on the rim of the cylinder 54 actuates a microswitch 66 by engaging its operating arm 66a. The microswitch is used to start the timing mechanism which times the coagulation period, the reaction being started by the insertion of the calcium chloride solution into the sample under test.

If desired, the pipette assembly described in co-pending application Ser. No. 775,252, filed Nov. 13, 1968, now U.S. Pat. No. 3,498,135, can be used. Also, the guide mechanism to be described in conjunction with FIG. 9 is convenient in permitting the end of the pipette to be properly placed over the top of the reciprocating test tube in the well 40.

It will be appreciated that while a sample is being tested, the magnetic member 18 effectively moves up and down through the sample, as mentioned above. The apparatus can be designed so that the movement of the magnetic member during the test extends from near the bottom of the test tube in the well to near the meniscus at the top of the fluid in the test tube. In this manner, and as pointed out previously herein, the magnetic member 18 also performs a mixing function, so that the liquids in the test tube are intimately mixed during the test. This mixing feature is especially important in certain tests referred to above involving, for example, kaolin. Kaolin is held in suspension in the liquid for certain tests, and it has a tendency to precipitate to the bottom of the test tube, this tendency being prevented by the mixing function established by the magnetic member.

The apparatus of the invention, in the embodiment under consideration, includes a simple known type of impulse counter which serves to record the prothrombin time during each sample test. The pulses for the counter can be conveniently generated by a pulse generator such as shown in FIG. 5. This pulse generator includes, for example, a simple magnetic reed switch 100 which is mounted on a base 102 by means, for example, of a pair of posts 104 and 106. A motor 108 is mounted under the base 102, and a drive shaft 110 from the motor extends through the base. A turntable 112 is supported on the upper end of the drive shaft under the reed switch 100, and a bar magnet 114 is mounted on the turntable adjacent the reed switch 100.

The field from the bar magnet 114 is such that the contacts of the reed switch are closed each time the bar magnet is disposed parallel to the longitudinal axis of the switch. This occurs twice for each revolution of the turntable 112. Therefore, there are two closures of the magnetic reed switch 100 for each revolution of the turntable 112. The turntable can be turned, for example, by the motor 108 at 300 rpm. This means that there are ten closures of the reed switch 100 per second, so that the pulse generator generates ten pulses per second. These pulses are generated by completing the circuit between the terminals 100a and 100b of the reed switch. The resulting generator represents an inexpensive mechanism, yet one which is precise and accurate.

For example, the motor 108 can be a synchronous motor, so that the repetition frequency of the pulses generated by the pulse generator is synchronized with the alternating current line frequency of the alternating current mains, and which is held precisely constant. Also, the reed switch 100 can be controlled, so that the pulse generator generates ten pulses per second, as mentioned above, so that the timing intervals can be timed with a resolution down to one-tenth of a second.

Referring now to the electrical diagram of FIG. 6, the circuit has a pair of input terminals 200 which are intended to be connected to the usual 115-volt alternating current mains. An appropriate neon indicating lamp and a series resistor 204 are connected across the terminals 200, the lamp 202 indicating when the circuit is energized.

The alternating current leads from the input terminals 200 are connected to the primary winding of a transformer 206. The transformer 206 serves to reduce the line voltage down to 24-volts a.c. The aforesaid light source 20 is connected across the secondary winding of the transformer 206. A bridge rectifier, made up of a group of diodes CR1, CR2, CR3, CR4 is connected to the secondary of the transformer 206, and this rectifier provides full-wave rectification of the alternating current, so as to establish 30-volts d.c. between the lead 208 and the grounded lead 210. A 500 microfarad filter capacitor C1 is connected across the leads.

The aforesaid heater 32 is connected through a usual thermostatic switch 212 across the 115 volt leads from the input terminals 200. A capacitor C2 of, for example, 0.01 microfarads, is connected between one of the aforesaid leads and the junction of the switch 212 and heater 23 to protect the contacts of the thermostatic switch. A neon indicator lamp 214 and series resistor 216 are connected across the heater 32, and this lamp glows whenever current is actually flowing through the heater. The indicator lamp 214 provides an indication as to when the block 30 of FIG. 2 has been brought up to operating temperature, at which time the lamp is extinguished.

The output of the photocell 22 is introduced to a photocell amplifier 217 which is made up of a pair of NPN transistors 218 and 220. The photocell is connected between the lead 208 and the base of the transistor 218. A 5 kilo-ohm potentiometer 222 connects the base of the transistor 218 to the grounded lead 210. The potentiometer can serve as a sensitivity adjustment for the output from the photocell. The collector of the transistor 218 is connected to the junction of a 15 kilo-ohm resistor 224 and an 820 ohm resistor 226. The resistor 224 is connected to the base of the transistor 220, whereas the resistor 226 is connected to the lead 208.

The base of the transistor 220 is connected to a 6.8 kilo-ohm resistor 228, whereas the emitter of the transistor 220, together with the emitter of the transistor 218, are connected to a 180 ohm resistor 230. The resistors 228 and 230 are both connected to the grounded lead 210. The collector of the transistor 220 is connected through the operating coil of a relay K1 to the positive lead 208. A diode CR5 is connected across the winding, and this diode serves to suppress the inductive transient from the relay winding and serves to protect the transistor 220.

The relay K1 has a pair of lower normally-open contacts and a pair of upper normally-open contacts. The lower normally-open contacts are connected to the lead 208 and relay coil K1 on one hand, and to the lower movable contacts of a relay K2 and to the start switch 66 on the other hand. It will be remembered that the start switch 66 is the microswitch of FIG. 2, and that this switch is closed the moment the calcium chloride is added to the liquid in the test tube to initiate the test. One side of the coil of the relay K2 is connected to the lower contacts and to the switch 66, and the other side of the coil of the relay K2 is grounded.

The upper contacts of the relay K1 are interposed in one of the alternating current leads from the input terminals 200 and to one terminal of each of the motors 44 and 108. The other terminal of each of these motors is connected to the other alternating current lead. Therefore, when the upper contacts of the relay K1 close, both the motors 44 and 108 are energized.

The upper contacts of the relay K2, on the other hand, when closed, serve to complete a connection to an impulse counter 250 which is in series with the magnetic reed switch 100, the other side of the impulse counter being connected to the positive lead 208. The impulse counter 250, for example, can be any known type of electromechanical counter having a numbered scale, and which provides a decimal reading of the number of pulses applied to it. The counter is preferably equipped with an appropriate reset lever. A diode CR6 is then connected across the impulse counter 250 to suppress inductive transients and to protect the reed switch 100.

When one of the test tubes 10 containing the magnetic ball 18 is dropped into the well 40 of the block 30 in FIG. 2, the ball is originally held by the magnets 14 and 16 between the light source 20 and the photocell 22. This causes the resistance of the photocell 22 to increase which, in turn, causes the photocell amplifier 217 to energize the relay K1. When the relay K1 is energized, the closure of its normally-open upper contacts energizes both the motors 108 and 44. Therefore, the moment the test tube is dropped into the well 40, the reciprocating motor 44 is energized and the test tube begins to move up and down in the well. In addition, the pulse generator motor 108 is energized at this time, so that the reed switch 100 is opened and closed at the rate, for example, of 10 closures per second. However, since the relay K2 is now de-energized, the pulses generated by the reed switch 100 are not counted by the impulse counter 250.

The moment the calcium chloride is introduced into the test tube in the well 40 to initiate the test, the switch 66 on the pipetting apparatus is closed momentarily. This causes the relay K2 to be energized through the lower closed contact of the relay K1. The lower contacts of the relay K2 now act as holding contacts, so that the relay K2 is held energized. So long as the relay K2 is energized, its upper contacts permit the pulses from the reed switch 100 to be passed to the impulse counter 250, so that the impulse counter performs a count of the said pulses.

The impulse counter 250 continues to count the pulses until the coagulation of the sample in the test tube moving up and down in the well 40 draws the ball 18 out of the magnetic field and out of the light beam from the source 20 to the photocell 22. When this occurs, the relay K1 becomes de-energized. This breaks the holding circuit to the relay K2, so that the relay K2 also becomes de-energized. Therefore, the pulses from the reed switch 100 are no longer applied to the impulse counter 250, and the impulse counter is stopped, thereby providing a reading of the prothrombin time.

Figure 8:
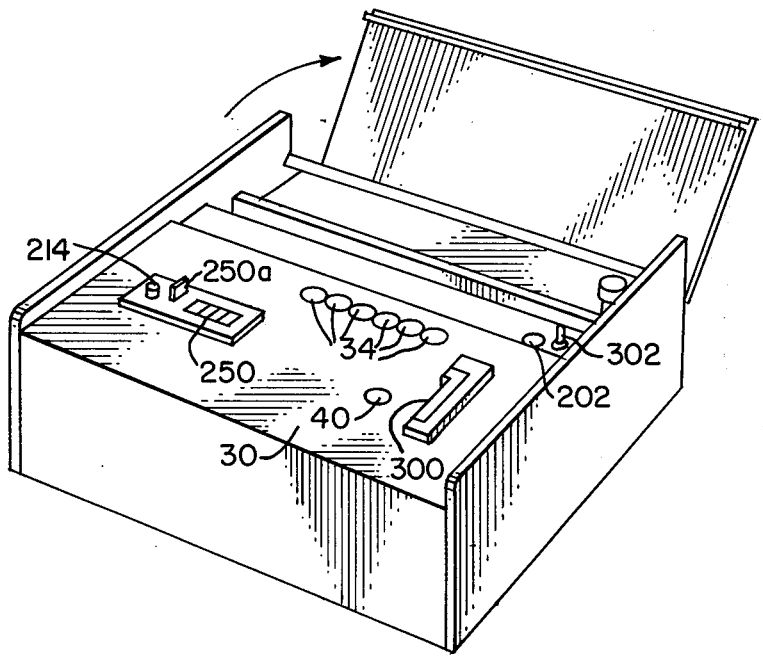

As mentioned above, the apparatus of the invention can be housed in a casing or other suitable supporting means such as shown in FIGS. 7 and 8. The block 30 is shown in FIGS. 7 and 8 with its incubation wells 34. Also the test well 40 is provided in the top of the block.

The impulse counter 250 is mounted so that its scale can be viewed through the case. A lever 250a can be provided for resetting the impulse counter scale back to zero, when so desired.

As mentioned above, the pulses from the pulse generator switch 100 permit the impulse counter 250 to provide decimal readings to one-tenth of a second. The neon indicator 214 is mounted adjacent the impulse counter and, as also explained, this indicator is extinguished when the block has been raised to the test temperature. The indicator lamp 202 is also provided to the right of the housing to indicate when the power is applied. An appropriate "on-off" toggle switch is mounted adjacent the indicator 202 to constitute the power switch for the unit.

A pipette mechanism 300, different from that described above, can be provided for adding the calcium chloride to the solution so as to initiate each test. This mechanism, for example, can be turned to a position over the well 40, at which time a measured quantity of calcium chloride is introduced into the moving test tube in the well 40, and the timer circuit is simultaneously started by closing a switch, such as the switch 66 in FIGS. 2 and 6, as described above.

Ancillary equipment such as pipettes and disposable tips, and the like, can be stored in a compartment formed in the rear of the casing, as shown in the view of FIG. 8. As mentioned above, instead of the pipette mechanism 300, the pipette described in co-pending application Ser. No. 775,252, filed Nov. 13, 1968, now U.S. Pat. No. 3,498,135, can be used to introduce the calcium chloride into the movable test tube in the well 40.

As mentioned above, the advantages and features of the apparatus, system and method of the present invention include the provision of a relatively inexpensive unit and method which can be operated easily and by semi-skilled personnel, and yet which is capable of quickly and accurately providing precise prothrombin time measurements, and the like. A major advantage of the apparatus described from an operational standpoint, is the fact that all the samples can be tested in disposable test tubes, so that there is no mess and no clean-up required after each test. The pipettes which are used to insert the blood or plasma samples into the test tubes, and which can be used to introduce the calcium chloride, can be equipped with removable tips, which can be discarded after each use.

The invention provides, therefore, an improved clot timer method, system and apparatus which operates on a viscosity principle, and which can be used in general, wherever viscosity levels above predetermined thresholds are to be sensed and/or corresponding time intervals for the test fluids to undergo viscosity changes are to be measured.

What is claimed is:

1. Apparatus for use in determining the prothrombin time of a blood sample comprising: a container for holding the blood sample, a freely movable ferromagnetic member disposed in the container, a magnetic field source located near the container and forming a weak magnetic couple with the ferromagnetic member, means for producing relative movement between the ferromagnetic member and the container; the intensity of the magnetic field source being sufficient to prevent relative movement between the ferromagnetic member and the magnetic field source prior to clotting but insufficient to prevent relative movement between the ferromagnetic member and the magnetic field source on clotting due to an increase in the resistance to movement of the ferromagnetic member in the container imposed on the ferromagnetic member by the blood sample, and means for deriving a signal in response to relative movement between the ferromagnetic member and the magnetic field source, the signal signifying the end point in determining the prothrombin time.

* * * * *